United States Patent
Westphal et al.

(10) Patent No.: US 7,072,047 B2
(45) Date of Patent: Jul. 4, 2006

(54) METHOD AND SYSTEM FOR QUANTITATIVE IMAGE CORRECTION FOR OPTICAL COHERENCE TOMOGRAPHY

(75) Inventors: Volker Westphal, Hanover (DE); Andrew M. Rollins, Highland Heights, OH (US); Joseph A. Izatt, Raleigh, NC (US)

(73) Assignees: Case Western Reserve University, Cleveland, OH (US); University Hospitals of Cleveland, Cleveland, OH (US)

( * ) Notice: Subject to any disclaimer, the term of this patent is extended or adjusted under 35 U.S.C. 154(b) by 17 days.

(21) Appl. No.: 10/619,574

(22) Filed: Jul. 14, 2003

(65) Prior Publication Data
US 2004/0068192 A1  Apr. 8, 2004

Related U.S. Application Data

(60) Provisional application No. 60/395,597, filed on Jul. 12, 2002.

(51) Int. Cl.
*G01B 9/02* (2006.01)
(52) U.S. Cl. ............................................. 356/497
(58) Field of Classification Search ............... 356/479, 356/497
See application file for complete search history.

(56) References Cited

U.S. PATENT DOCUMENTS 6,293,674 B1  9/2001  Huang et al. ............... 351/221

FOREIGN PATENT DOCUMENTS

WO  03/011764 A2  2/2003

OTHER PUBLICATIONS

International Search Report—PCT/US03/21898, Dated Dec. 15, 2003, International Filing Date Jul. 14, 2003.
Siavash Yazdanfar, Andrew M. Rollins and Joseph A. Izatt—Imagine and Velocimetry of the Human Retinal Circulation with color Doppler Optical Coherence Tomography, from Optics Letters/ vol. 25, No. 19, Oct. 1, 2000, XP-002263092.
E.A. Swanson, J.A. Izatt, M.R. Hee, D. Huang, C.P. Lin, J.S. Schuman, C.A. Puliafito and J.G. Fujimoto—In Vivo Reginal Imaging By Optical Coherence Tomography, May 27, 1993, XP-002102402.

(Continued)

*Primary Examiner*—Hwa (Andrew) Lee
(74) *Attorney, Agent, or Firm*—Renner, Otto, Boisselle and Sklar, LLP

(57) ABSTRACT

A method of correcting optical coherence tomography (OCT) image data obtained from a layered media sample includes identifying at least one interface from the obtained OCT data and correcting the OCT data for distortion at the at least one interface. The OCT image data can be corrected for extrinsic distortions, such as those caused by scan geometry, as well as, intrinsic distortions, such as those caused by refraction at each interface.

17 Claims, 8 Drawing Sheets

OTHER PUBLICATIONS

Joseph A. Izatt, Siavash Yazdanfar, Volker Westphal, Sunito Radhakrishnan and Andrew M. Rollins, Real-time and Functional Optical Coherence Tomography, pp. 110-112.

Volker Westphal, Sunita Radhakrishnan, Andrew M. Rollins and Joseph A. Izatt, Quantitative OCT Image Correction Using Fermat's Principle and Mapping Arrays, Proceedings of SPIE vol. 4619 (2002) pp. 54-58, XP008013346.

V. Westphal, A.M. Rollins, S. Radhakrishnan, J. A. Izatt, "Correction of geometric and refractive image distortions in optical coherence tomography applying Fermat's principle," Optics Express, 10 (9), 397-404 (May 6, 2002).

METHOD AND SYSTEM FOR QUANTITATIVE IMAGE CORRECTION FOR OPTICAL COHERENCE TOMOGRAPHY

CROSS-REFERENCE TO RELATED APPLICATIONS

This application claims priority under 35 U.S.C. §119 from Provisional Application Ser. No. 60/395,597 filed Jul. 12, 2002, the entire disclosure of which is incorporated herein by reference.

TECHNICAL FIELD

The present invention relates generally to the field of optical coherence tomography and, more particularly, to a method and system for quantitative image correction of optical coherence tomography images of layered media.

BACKGROUND

Optical coherence tomography (OCT) is a technology that allows for non-invasive micron-scale resolution imaging in living biological tissues. Recent OCT research has focused on developing instrumentation appropriate for imaging in clinical settings (e.g., in ophthalmology, dermatology and gastroenterology), on resolution improvements, real-time imaging, and on functional imaging, such as in color Doppler OCT.

Current-generation real-time OCT systems typically employ depth-priority scanning, with the axial scan implemented using a rapid-scan optical delay (RSOD) in the reference arm. The rapid axial scan is readily implemented using resonant scanners. However, the resulting sinusoidally varying delay axially distorts the resulting OCT imagines. In addition, the use of non-telecentric scan patterns is often necessitated by non-planar sample configurations (e.g., imagining the convex surface of the cornea or the concave surface of a hollow organ or tract).

One major impediment to the use of OCT for quantitative morphological imaging is image distortions that may occur due to several mechanisms, including nonlinearities in the reference or sample scan mechanisms, non-telecentric (diverging or converging) scan geometries, and the refraction of probe light in the sample. Non-contact imaging, one of the primary advantages of OCT, also leads to significant image distortions due to refraction of the probe beam at the interface between air and smooth surfaces, such as the cornea, or liquid accumulations in internal organs. Image distortions due to refraction may also occur at internal smooth tissue index boundaries, such as the cornea-aqueous interface in the eye.

Accordingly, a need exists for an improved method and system for quantitative imagine correction of OCT images, which overcome the above-referenced problems and others.

SUMMARY OF THE INVENTION

According to one aspect of the invention, the invention is directed to a method of correcting optical coherence tomography (OCT) data obtained from a layered media having at least one interface. The method can include identifying the at least one interface from the obtained OCT data and correcting the OCT data for distortion at the at least one interface.

According to another aspect of the invention, the invention is directed to a quantitative image correction method for optical coherence tomography (OCT). The method can include correcting for external distortions caused by scan geometry and correcting for intrinsic distortions within a sample.

According to another aspect of the invention, the invention is directed to a non-invasive system for imaging an anterior portion of an eye. The system can include an optical coherence tomography (OCT) data acquisition system and an OCT data correction processor, which (i) receives OCT data from the OCT data acquisition system, (ii) automatically segments anatomical structures in the anterior portion of the eye to detect at least one interface, and (iii) corrects for refraction effects at the at least one detected interface.

According to another aspect of the invention, the invention is directed to a non-invasive method for imaging an anterior portion of an eye. The method can include obtaining optical coherence tomography (OCT) data from the eye. From the obtained OCT data, a position of (i) the epithelium, (ii) the endothelium and (iii) the iris can be determined. Image data distortions caused by at least one of (i) a first interface including the epithelium and (ii) a second interface including the endothelium can be corrected.

BRIEF DESCRIPTION OF DRAWINGS

These and further features of the present invention will be apparent with reference to the following description and drawings, wherein.

DISCLOSURE OF INVENTION

Figure 1:
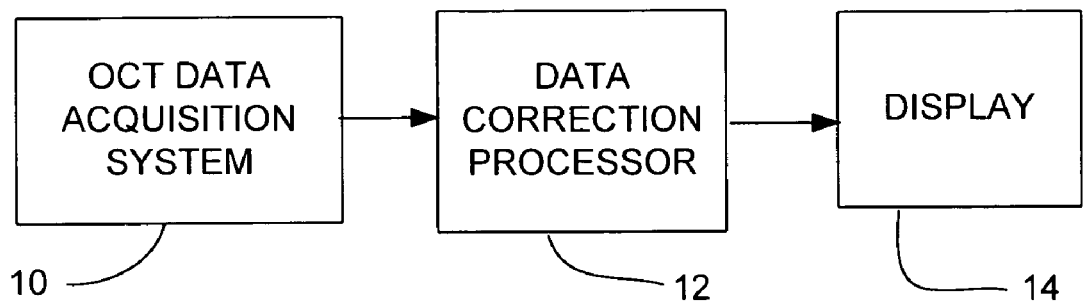
FIG. 1 is a schematic illustration of a non-invasive imaging system for use in accordance with the present invention.

In the detailed description that follows, corresponding components have been given the same reference numerals regardless of whether they are shown in different embodiments of the present invention. To illustrate the present invention in a clear and concise manner, the drawings may not necessarily be to scale and certain features may be shown in somewhat schematic form.

With reference to FIG. 1, a non-invasive optical imaging system is provided. In one embodiment, the system includes an optical coherence tomography (OCT) system 10. Raw or otherwise uncorrected OCT data is transmitted to a data correction processor 12. As is discussed more fully below, the data correction processor 12 can correct for both external distortions (e.g., distortions relating to the scan geometry) and intrinsic distortions within the sample (e.g., refraction). The corrected or target OCT data can then be presented on a human-readable display 14 for use in determining and/or evaluating diagnostic parameters.

Figure 2:
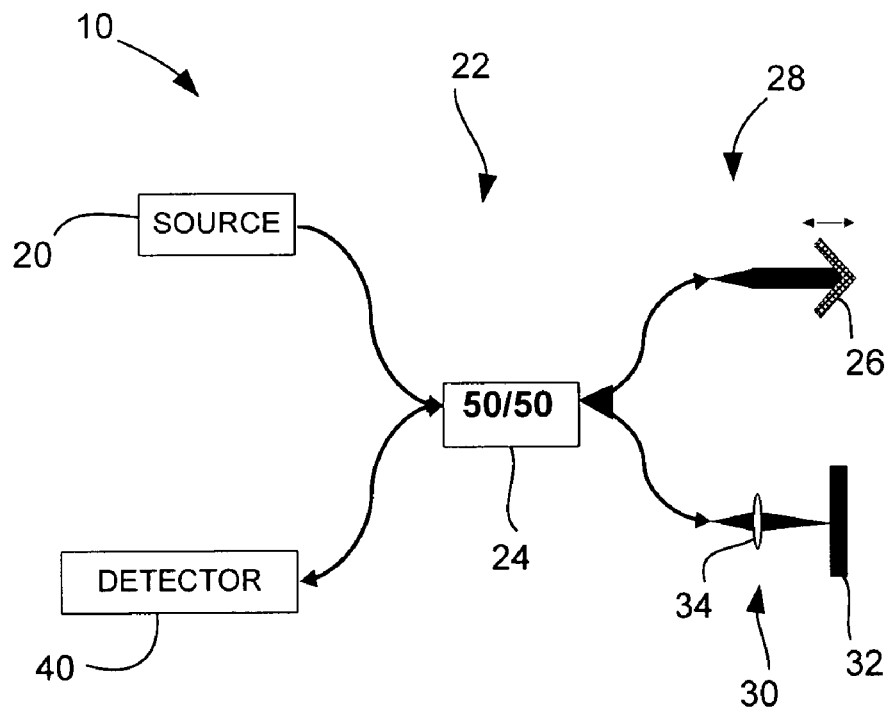
FIG. 2 is a schematic illustration of an exemplary optical coherence tomography (OCT) imaging system for use in accordance with the present invention.

FIG. 2 illustrates an exemplary OCT data acquisition system 10, which can be used in connection with the present invention. In one embodiment, the OCT data acquisition system 10 includes a source 20, such as a super-luminescent diode (SLD) source. The optical radiation or light source 20 can illuminate an OCT interferometer 22, which can include a beam splitter 24 (such as a fused-taper 50/50 fiber coupler). The beam splitter 24 separates the optical radiation received from the source 20 into two beams. It is to be appreciated that the beam splitter could be other then a 50/50 or balanced fiber coupler, such as an unbalanced fiber coupler (e.g., $\alpha/(1-\alpha)$). Optical radiation can be transmitted to a reference arm 28, including a reference element 26, such as a translating or rotating reference mirror. The other beam can be transmitted to a sample arm 30, optionally including a beam-steering mirror 30, to focus the combined optical radiation on a sample 32. The reflected light received by the beam splitter 24, back from both the reference arm 28 and sample arm 30 is combined and transmitted to one or more detectors 40, such as photoreceivers or photodetectors.

Figure 3:
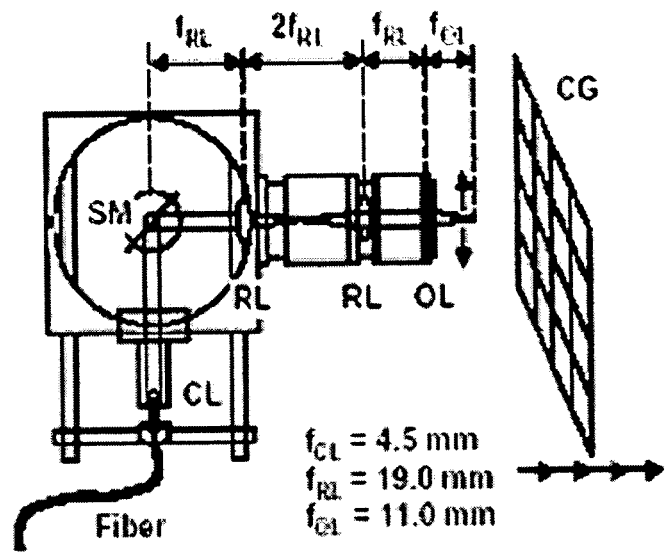
FIG. 3 is a schematic illustration of an exemplary lateral scanning hand held probe for use in accordance with the present invention.

It is to be appreciated that a variety of OCT data acquisitions and data acquisition devices can be employed without departing from the scope of the present invention. For example, FIG. 3, schematically illustrates an exemplary lateral scanning handheld probe with a diversion scan. Such an OCT system can include a Fourier-domain rapid-scanning optical delay (RSOD) in the reference arm incorporating a resonant scanner oscillating at 2 kHz. For the sake of illustration it is to be appreciated that the following abbreviations are used in FIG. 3; CL—Collimation Lens, SM—Scanning Mirror, RL—Relay Lens, OL—Objective Lens, CG—Calibration Grid, $f_{xx}$—Focal Length of Lens XX.

Figure 4:
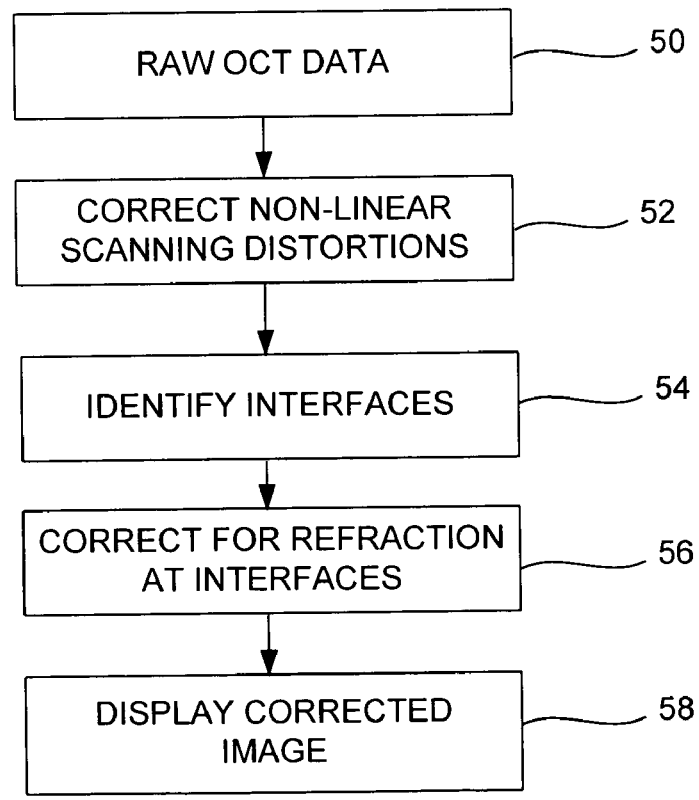
FIG. 4 is a flow chart illustrating a method for correcting extrinsic and intrinsic distortions in OCT data in accordance with the present invention.

With reference now to FIG. 4, a method for correcting distortions in optical coherence tomography (OCT) data is provided. The method begins at step 50 with the correction of uncorrected or raw OCT data. It is to be appreciated that, in accordance with one embodiment, the method finds applicability to correcting both external distortions (such as those caused by scan geometry) and intrinsic distortions within the sample (such as those found in layered media or samples). At step 52, the raw OCT data can be corrected for non-linear scanning distortions. Such distortions can include non-linear axial scanning distortions, non-linear lateral scanning distortions and/or non-telecentric scanning distortions.

Figure 5:
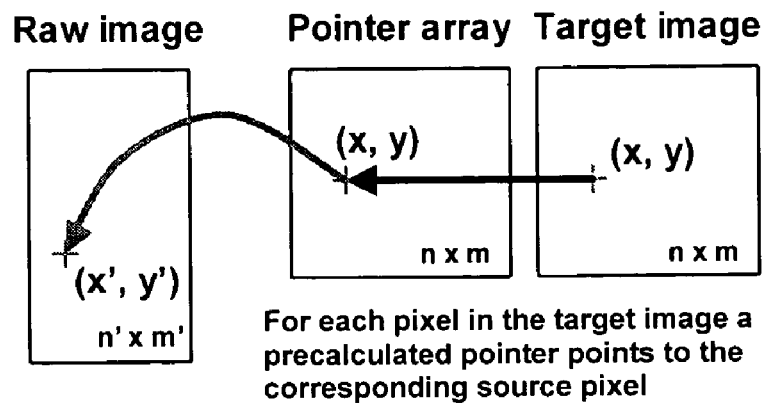
FIG. 5 is a schematic illustration of a mapping array for use in accordance with the present invention.

In one embodiment, image transformations can be implemented using either forward or backward mapping approaches. In the raw (uncorrected) OCT image, x' and y' can be defined to denote the coordinates across and along A-scans (single depth scans). x and y are the corresponding coordinates in the target (corrected) image (see FIG. 5). Pixel positions are abbreviated as P'=(x',y') and P=(x,y). A forward mapping approach (P=f(P')) calculates the target position for a given raw image data point. Since the target position P will most likely fall between target pixels, algorithms can be applied to distribute the value of the raw image pixel onto several neighboring pixels. Since the density of this distribution is in general nonhomogeneous, the brightness of the target image must be renormalized, which can be a significant computational expense.

A backward mapping approach (P'=F(P)) avoids this disadvantage by mapping each target pixel to a location in the raw image, then uses simple interpolations between surrounding pixels in the raw image to obtain the target pixel value. Furthermore, the number of transformations is at the optimum of one per target pixel, another advantage compared with forward mapping. If the same backward transformation is applied to all images, it can be implemented with lookup table (also referred to as a pointer array or mapping array) to achieve real-time imaging.

Transformations can be cascaded, using the output of one transformation as the input for the next.

Figure 6:
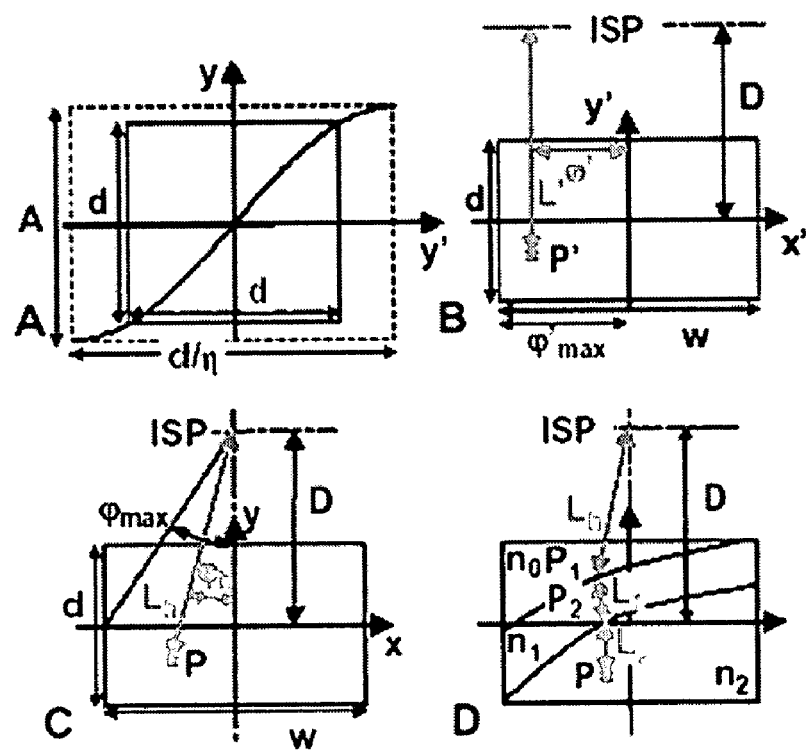
FIG. 6A is a plot schematically illustrating correction of non-linear axial scanning.
FIG. 6B is a schematic illustration of a coordinate system for raw OCT image data.
FIG. 6C is an exemplary schematic target coordinate system in a homogeneous medium.
FIG. 6D is an exemplary schematic illustration of refractive interfaces in a sample altering ray paths.

With reference to FIG. 6 and continued reference to FIG. 4, in one embodiment, the step of correcting non-linear scanning distortions 52 can include correcting distortions due to non-linear axial scanning. The motion of the resonant scanner can be well described as sinusoidal, simplifying the backward transformation. In a standard high-speed OCT system the carrier is generated by the scan mirror motion. Therefore, the nonlinear motion also limits the usable duty cycle $\eta$ if no tracking filters are employed. Within this duty cycle, the scan depth d is acquired. With this knowledge, the forward transformation for the axial scan coordinate y can be written as (FIG. 6A)

$$y = f_{res,y}(x', y') = A\sin\left(\pi\eta\frac{y'}{d}\right) \quad (1)$$

The total scan depth A can be calculated from $$f_{res,y}\left(x' \cdot \frac{d}{2}\right) = \frac{d}{2} \quad (2)$$

$$A = \frac{d}{2}\sin^{-1}\left(\frac{\pi\eta}{2}\right). \quad (3)$$

Therefore, the backward transformation can be written as $$x'=F_{res,x}(x,y)=x \quad (4)$$

$$y' = F_{res,y}(x, y) = \frac{d}{\pi\eta}\arcsin\left(\frac{y}{A}\right). \quad (5)$$

since the horizontal scan is linear. The transformations to correct non-telecentric scanning and refraction can use the target image of this transformation as the raw image or the transformations can be analytically cascaded.

To correct for geometric image distortions due to non-telecentric scanning, the coordinate systems for the raw and target images are defined in terms of the scan geometry (FIG. 6B, 6C). It can be assumed that the OCT image is formed using a sample arm probe that incorporates a rotating mirror scanner [2]. The origin for both systems is in the center of the image. x' is linear with acquisition time and thereby with the lateral scanning mirror movement. The center of the field of view (FOV, having width w and depth d) is a distance D from the scanning pivot (SP) or an image of the sample pivot (ISP), depending upon the internal details of the sample arm probe. For positive or negative D, scans diverge or converge, respectively. For telecentric scans, D approaches infinity, but for any real system, this can always be approximated by a large D.

The target pixel position P can also be defined in polar coordinates (φ, L), with the scanning angle φ in the FOV and the distance L from ISP to P (FIG. 6B, 6C). For a homogeneous sample without refraction (denoted by subscript h), φ and L are given by $$\phi_h(x,y) = \arctan(x/(D-y)). \quad (6)$$

and $$L_h(x,y) = D - \sqrt{x^2 + (D-y)^2}. \quad (7)$$

The scanning angle to reach the extreme of the FOV at the center plane is given by $\phi_{max} = \phi_h$. In the rectangular array of acquired data, the scan angle φ' in the FOV is linear with position x': $\phi'(x', y') = 2x'\phi'_{max}/W = x'D$, while the distance between ISP and P' is $L'(x', y') = D - y'$. Since $\phi = \phi'$, $L = L'$, and $\phi_{max} = \phi'_{max}$, the complete backward transformations are given by:

$$x' = F_{xh}(x, y) = \arctan\left(\frac{x}{D-y}\right) \cdot D \quad (8)$$

$$y' = F_{yh}(x, y) = D - \sqrt{x^2 + (D-y)^2} \quad (9)$$

It is to be appreciated that the step of correcting non-linear scanning distortions 52 may be performed at various times during the correction process or not at all.

Figure 7:
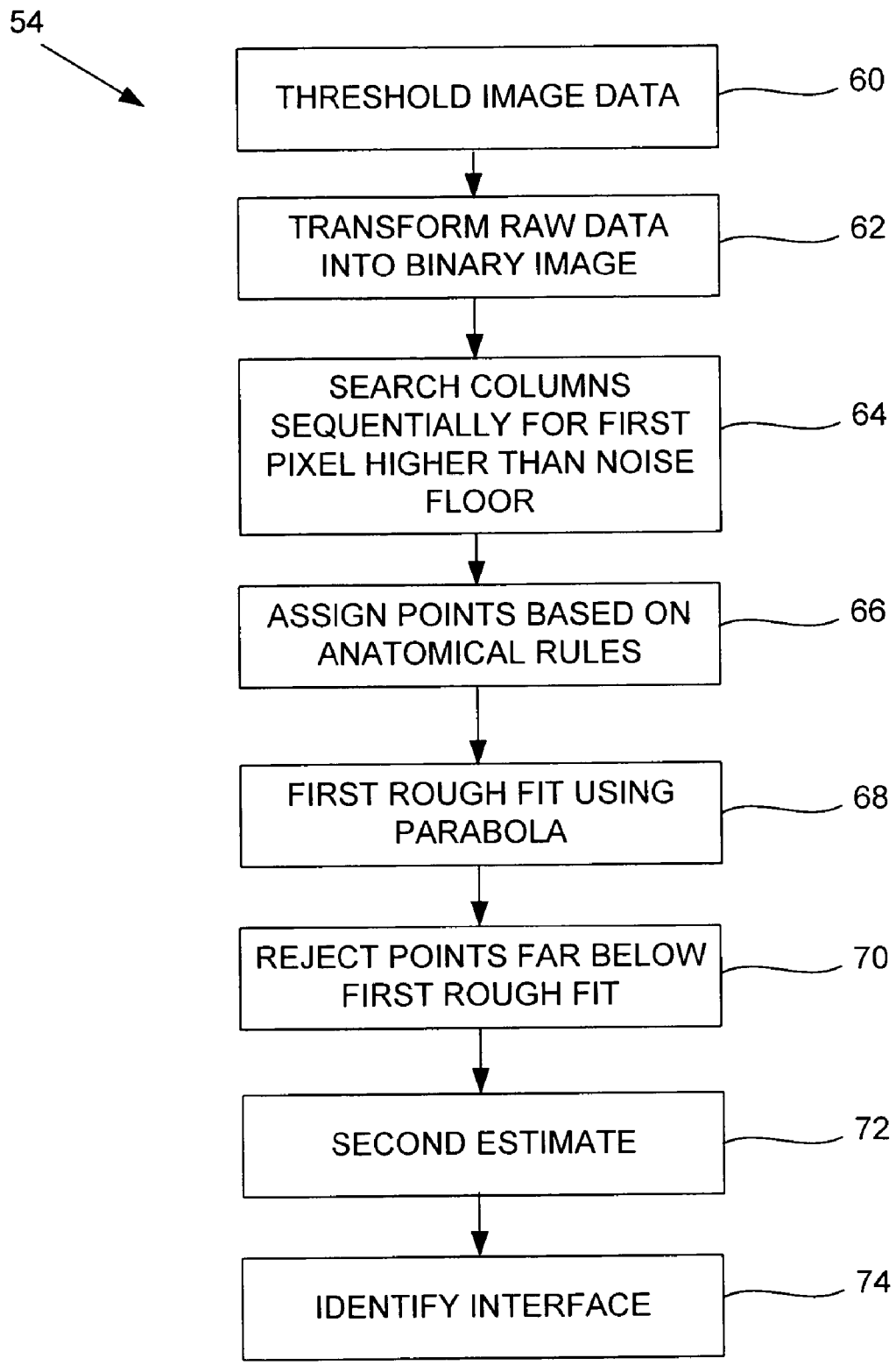
FIG. 7 is a flow chart illustrating a method of identifying interfaces within the sample in accordance with the present invention.

Referring again to FIG. 4, at step 54, the raw OCT data or the OCT data corrected for non-linear scanning distortions can be processed to identify any interfaces present within the sample. As shown in FIG. 7, identifying the interfaces 54 can include thresholding the image data 60. In one embodiment, the image data can be thresholded four standard deviations above the noise floor. Alternatively, other appropriate thresholding can be performed in order to remove most "salt and pepper noise" from the image data. Following the thresholding step 60, the raw image data can be transformed into a binary image 62 using known techniques.

Once the image data has been transformed into binary image data, the image data can be searched sequentially 64, e.g., on a column-by-column basis. In searching the image data 64, positive and negative transitions are sought as indicators of the existence of upper and lower interface boundaries. For example, a column of data can be searched wherein each pixel is compared to a threshold indicative of the noise floor for the image data. Once a pixel having a value higher than the noise floor is found, that pixel is assigned as a potential interface boundary. As the columns of data are searched, interface data points are assigned 66 based upon predetermined anatomical rules. For example, in the case of imaging the anterior segment of the eye, certain anatomical rules are known. These rules include: (a) the epithelial and endothelial interfaces are smooth curves that are, to a first approximation, parabolic; (b) the epithelial and endothelial interfaces are both concave inward; (c) the endothelial interface lies at least 0.3 mm below the epithelial interface; (d) the iris is disposed below the endothelial interface; (e) an anterior chamber is greater than about 0.1 mm deep, said endothelial interface and said iris meeting in the anterior chamber angles; and (f) a lens capsule is apparent within the iris lumen. Of course, other anatomical rules could be applied depending on the particular imaging application.

Therefore, in the above ocular example, the columns of data can be searched and the first data point determined to be above the noise floor is assigned as a potential point indicative of the epithelium or epithelial interface (i.e., the upper surface of the cornea). Once the potential interfaces are located as set forth in step 66, a first predetermined geometric fit is applied 68 to the assigned interface points of the interfaces. In the ocular example, a parabolic fit is applied to the interface points assigned to the epithelium. Of course, other geometric fits could be applied depending upon the predetermined anatomical rules associated with the particular imaging application.

After the first geometric fitting step 68, a plurality of rejection rules are applied 70 to the assigned interface points. These rejection rules can be based on predetermined anatomical rules and knowledge in connection with the particular imaging application. For example, in the case of imaging the anterior segment of the eye, certain rejection rules can be applied. These rules include: (a) reject interface data points more than a predetermined distance apart from the first parabolic fit; (b) reject data points without immediate left and right neighboring data points; (c) reject data points that, along with neighboring data points, are within a top 0.1 mm of the overall image; (d) reject iris points about estimated endothelial and epithelial interfaces and below estimated iris; and (e) for iris data points, replace vertical positions by the median of neighborhood data points. Of course, other rejection rules could be applied depending upon the predetermined anatomical rules associated with the particular imaging application. It is to be appreciated that the above rejection rules could be applied through one or more iterations in which tolerances for rejected points are steadily and progressively decreased.

After the plurality of rejection rules are applied 70, a second predetermined geometric fit 72 can be applied to the remaining assigned interface points to provide a second estimate of the interface or corresponding interface structure. In the ocular example discussed herein, the second fit could be another parabolic fit or, alternatively, a quadrabolic fit. This second fit and/or estimate 72 should identify the present interface 74.

Returning to the example of imaging the anterior segment of the eye, the above-described methodology for identifying interfaces (illustrated in FIG. 7) would also be repeated for the endothelium or endothelial interface, which comprises the lower boundary of the cornea.

Figure 8:
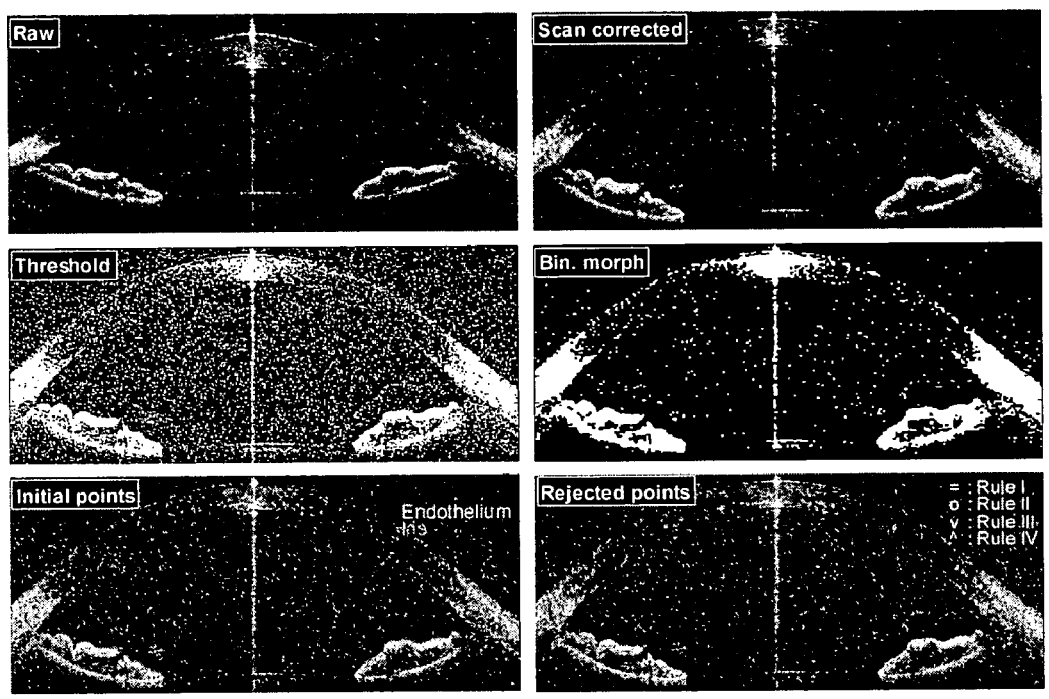
FIG. 8 illustrates an exemplary series of OCT images corrected in accordance with the present invention.

By way of example, FIG. 8 provides exemplary images illustrating the methodology described in FIG. 4 and FIG. 7 in connection with an ocular example described above. For example, raw OCT data (upper left image) is corrected for non-linear scanning distortions (upper right image). The image is thresholded (middle left image) and binary morphed (middle right image). The initial points are identified and assigned (bottom left image) and then certain points are rejected (bottom right image).

In addition, it is to be appreciated that the interface identifying (also referred to as segmentation) methodology discussed above and illustrated in FIG. 7, can provide useful information about the anterior segment and chamber of the eye. This information can be employed in a number of diagnostic applications, including, but not limited to determination of angle parameters related to the intersection of the endothelium and the iris, which can be useful in evaluating the risk of acute angle-closure glaucoma, and the exact fitting of intraocular lenses. Appositional angle closure is a risk factor for progressive trabecular damage, elevated intraocular pressure and acute angle-closure glaucoma. Phakic intraocular lenses (IOL) are a relatively new class of devices implanted to correct severe myopia and hyperopia. The exact dimensions of the anterior chamber (AC) must be known to determine the lens size for a correct fit. In accordance with the methodologies discussed herein, OCT is capable of rapidly imaging the complete AC with a resolution of about 10 microns.

Figure 9:
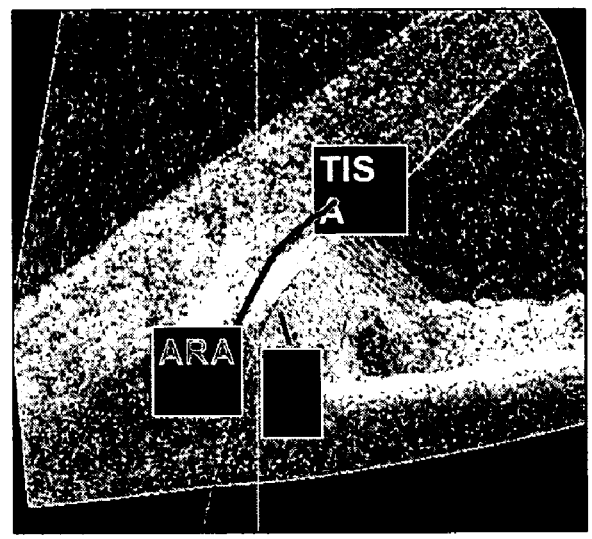
FIG. 9 illustrates an exemplary image to be used for diagnosing risk of acute angle-closure glaucoma
Figure 10:
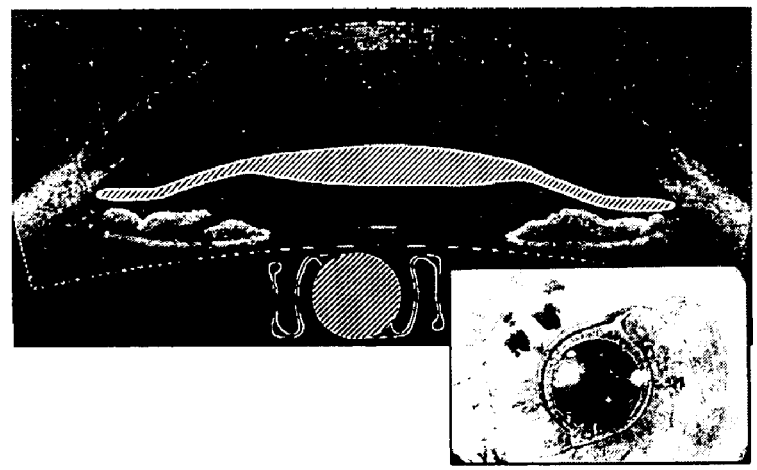
FIG. 10 illustrates an exemplary image to be used for exact fitting of an intraocular lens.

FIG. 9 and FIG. 10 provide exemplary images relating to diagnosing risk of acute angle-closure glaucoma (FIG. 9) and exact fitting of intraocular lenses (FIG. 10).

Referring again to FIG. 4, once the interfaces within the sample (e.g., the epithelial interface and the endothelial interface) have been identified 54, this information can be used to provide correction for the internal distortion 56 (e.g., refraction) caused by these interfaces. While the present invention is most concerned with correction of refraction effects caused by interfaces within the sample, it is to be appreciated that the present invention may be amenable to correction of other intrinsic distortions, such as diffraction and the like.

In order to correct for refraction, the refractive indices of sample layers must be known and the interfaces between them must be identified (FIG. 6D). Then, fundamental principles can be applied to correct for beam deflection and to transform optical into physical pathlengths. In the following, it is assumed k layers of different media in the image area, having indices of refraction $n_1$ to $n_k$, with the probe beam entering the sample from the top of the image in air ($n_0=1$). The interfaces $I_k(x)$ between layers of differing index are assumed to be smooth functions.

In one embodiment, a forward transformation for refraction correction could use Snell's law to calculate the target pixel for each raw data pixel, by propagating the incident beam sequentially through the sample layers and keeping track of optical path length until the correct distance is reached. However, the raw image is distorted by the scan geometry and refraction on previous interfaces. Therefore, defining the normal on the interface and the incident angle to apply Snell's law becomes very complicated in raw image coordinates. For the backward transformation, the interfaces can be defined distortion-free in target coordinates, avoiding this difficulty. However, for the latter transformation, Snell's law cannot be applied since the route of the beam through the sample is not known a priori. A solution can be obtained, however, by applying Fermat's principle, which states that light rays will propagate such that the optical path between source and target locations is minimized. Assuming the sample beam passes though the points Pi at the interfaces of the layers to reach P (FIG. 6D), the total optical pathlength is the sum of the distance from ISP to $P_1$ (Eq. (7)) and the optical path between subsequent Pi's to P:

$$L(P_1 \ldots P_k, P) = L_h(P_1) + \sum_{i=1}^{k-1} n_i |P_i P_{i+1}| + n_x |P_k P|. \quad (10)$$

By varying the location of $P_i$ along the interfaces, a minimum of L can be found, satisfying Fermat's principle. Assuming the paths of the different probe beams do not cross within the FOV, a unique solution exists for the $P_i$. After iteratively solving for the values of $P_i$, the complete back transformation can be written as $$x' = F_x(P_1, \ldots, P_k, P) = F_{xh}(P_1). \quad (11)$$

$$y' = F_y(P_1, \ldots, P_x, P) = D - L(P_1, \ldots, P_x, P). \quad (12)$$

Figure 11:
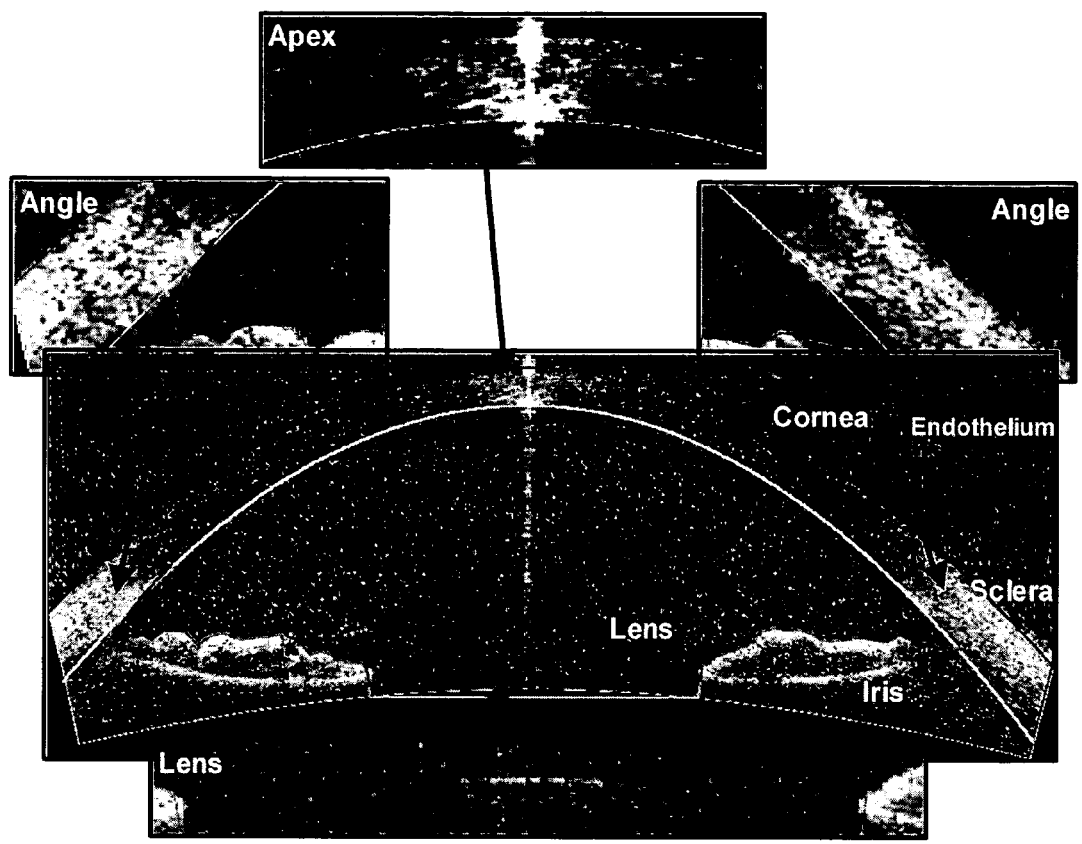
FIG. 11 illustrates exemplary images of the anterior segment of the eye, including the epithelium, endothelium, iris, lens and angular portion, corrected in accordance with present invention.

Referring again to FIG. 4, once the OCT data has been corrected for refraction 56 or other distortions at the interfaces, the corrected image can be displayed. FIG. 11 provides an exemplary image of the anterior chamber of the eye, including the cornea (defined by the epithelium and endothelium), the iris, the angular chambers and the lens. As described above, the position of the detected epithelium and endothelium of the cornea were used for refraction correction. The angle portions of the anterior chamber can be detected and refined using a dynamic programming technique. Because the mechanics of dynamic programming are known to skilled artisans, the details will not be discussed herein.

Figure 12:
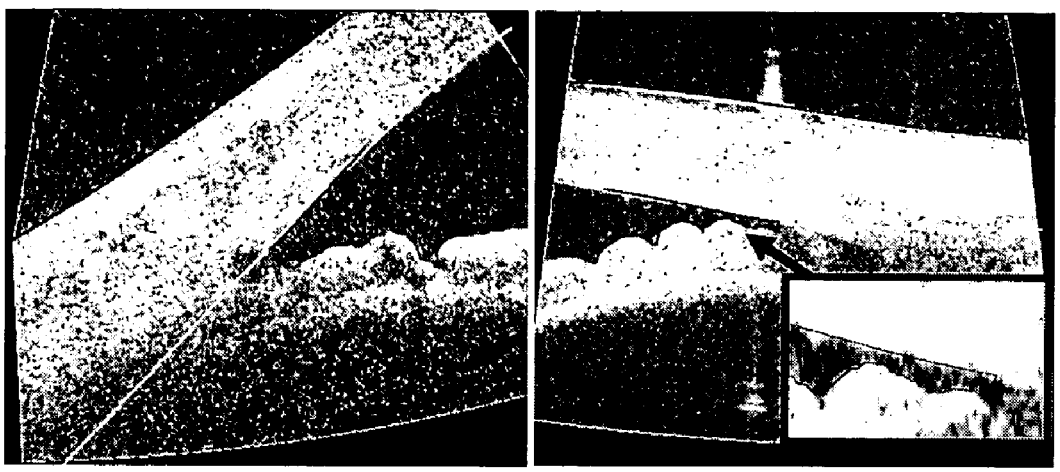
FIG. 12 illustrates exemplary partial images of the anterior segment corrected in accordance with the present invention.

As shown in FIG. 12, the present invention is insensitive to partial views such that only part of the anterior segment need be imaged (e.g., with a handheld scanner). These partial views are processed in the same manner described more fully above.

Although, particular embodiments of the invention have been described in detail, it is understood that the invention is not limited correspondingly in scope, but includes all changes, modifications, and equivalents coming within the spirit and terms of the claims appended hereto. In addition, it is to be appreciated that features shown and described with respect to a given embodiment may also be used in conjunction with other embodiments.

What is claimed is:

1. A method of correcting optical coherence tomography (OCT) data obtained from a layered media having at least one interface, the method comprising:
   from the obtained OCT data, identifying the at least one interface; and
   correcting the OCT data for distortion at the at least one interface, wherein identifying the at least one interface includes:
   transforming the obtained OCT data into a binary image;
   searching a plurality of OCT image data columns sequentially for upper and lower boundaries of the at least one interface;
   based on the searching step, assigning interface data points based on a set of predetermined rules regarding the at least one interface;
   applying a first predetermined geometric fit to the assigned interface points of the at least one interface;
   applying a plurality of predetermined rejection rules to the assigned interface points;
   rejecting assigned interface points according to the predetermined rejection rules; and
   applying a second predetermined geometric fit to any remaining assigned interface points.

2. The method according to claim 1, wherein the distortion at the at least one interface is refraction.

3. The method according to claim 2, wherein correcting the OCT data for refraction includes:
determining a minimum optical pathlength for a plurality of points corresponding to the obtained OCT data; and
transforming the determined minimum optical pathlength into a physical pathlength.

4. The method according to claim 3, wherein the transforming step includes a backwards transformation.

5. The method according to claim 2, further comprising:
removing image distortions due to at least one of (i) nonlinear axial scan velocity, (ii) nonlinear lateral scan velocity, and (iii) non-telecentric scan geometry.

6. The method according to claim 2, wherein the OCT data is corrected using one of (i) forward mapping and (ii) backward mapping.

7. The method according to claim 3, wherein the layered media is the eye.

8. The method according to claim 7, wherein the at least one interface includes an epithelial interface.

9. The method according to claim 8, wherein the at least one interface further includes an endothelial interface.

10. A method of correcting optical coherence tomography (OCT) data obtained from an eye having at least an epithelial interface and an endothelial interface, the method comprising:
from the obtained OCT data, identifying at least one of the epithelial interface and the endothelial interface; and
correcting the OCT data for refraction at at least one of the epithelial interface and the endothelial interface, wherein identifying at least one of the epithelial interface and the endothelial interface includes:
transforming the obtained OCT data into a binary image;
searching a plurality of OCT image data columns sequentially for (i) the epithelial interface, (ii) the endothelial interface, and (iii) the iris;
based on the searching step, assigning data points as being indicative of the epithelial interface based on a set of predetermined ivies regarding the (i) epithelial interface, (ii) the enciothelial interface, and (iii) the iris;
applying a first parabolic fit to the assigned data points indicative of the epithelial interface;
applying a plurality of predetermined rejection rules to the assigned interface points;
rejecting assigned interface points according to the predetermined rejection rules; and
applying one of (i) a second parabolic fit and (ii) a quadrabolic fit to any remaining assigned interface points, said fit being indicative of the epithelial interface.

11. The method according to claim 10, wherein the predetermined rules regarding the (i) epithelial interface, (ii) the endothelial interface, and (iii) the iris include at least one of the following:
(a) the epithelial and endothelial interfaces are smooth curves that are, to a first approximation, parabolic;
(b) the epithelial and endothelial interfaces are both concave inward;
(c) the endothelial interface lies at least 0.3 mm below the epfthelial interface;
(d) the iris is disposed below the endothelial interface; (e) an anterior chamber is greater than about 0.1 mm deep, said endothelial interface and said iris meeting in the anterior chamber angles; and
(f) a lens capsule is apparent within the iris lumen.

12. The method according to claim 11, wherein the predetermined rejection rules include at least one of the following:
(a) reject interface data points more than a predetermined distance apart from the first parabolic fit;
(b) reject data points without immediate loft and right neighboring data points;
(c) reject data points that, along with neighboring data points, are within a top 0.1 mm of the overall image;
(d) reject iris points about estimated endothelial and epithelial interfaces and below estimated iris; and
(e) for iris data points, replace vertical positions by the median of neighborhood data points.

13. The method according to claim 10, wherein transforming the obtained OCT data into a binary image includes:
thresholding the data points about four standard deviations above a determined noise floor.

14. A quantitative image correction method for optical coherence tomography (OCT), the method comprising:
correcting for external distortions caused by scan geometry; and
correcting for intrinsic distortions within a sample by identifying the at least one interface in the OCT image and correcting OCT data for distortion at the at least one interface, wherein identifying the at least one interface includes:
transforming the obtained OCT data into a binary image;
searching a plurality of OCT image data columns sequentially for upper and lower boundaries of the at least one interface;
based on the searching step, assigning interface data points based on a set of predetermined rules regarding the at least one interface;
applying a first predetermined geometric fit to the assigned interface points of the at least one interface;
applying a plurality of predetermined rejection rules to the assigned interface points;
rejecting assigned interface points according to the predetermined rejection rules; and
applying a second predetermined geometric fit to any remaining assigned interface points.

15. A non-invasive system for imaging an anterior portion of an eye, the system comprising:
an optical coherence tomography (OCT) data acquisition system; and
an OCT data correction processor which (i) receives OCT data from the OCT data acquisition system, (ii) automatically segments anatomical structures in the anterior portion of the eye to detect at least one interface, and (iii) corrects for refraction effects at the at least one detected interface, wherein the OCT data correction processor automatically segments anatomical structures in the anterior portion of the eye to detect at least one interface by:
transforming the obtained OCT data into a binary image;
searching a plurality of OCT image data columns sequentially for (i) the epithelial interface, (ii) the endothelial interface, and (iii) the iris;
based on the searching step, assigning data points as being indicative of the epithelial interface based on a set of predetermined rules regarding the (i) epithelial interface, (ii) the endothelial interface, and (iii) the iris;
applying a first parabolic fit to the assigned data points indicative of the epithelial interface;

applying a plurality of predetermined rejection rules to the assigned interface points;

rejecting assigned interface points according to the predetermined rejection rules; and applying one of (i) a second parabolic fit and (ii) a quadrabolic fit to any remaining assigned interface points, said fit being indicative of the epithelial interface.

16. The system according to claim 15, wherein the OCT data acquisition system includes:

an optical radiation source;

a reference arm and a sample arm each coupled to the optical radiation source via a beam splitter; and a detector coupled to the beam splitter for receiving optical radiation from the sample arm and the reference arm.

17. The system according to claim 15, wherein the OCT data correction processor removes image distortions due to at least one of (i) nonlinear axial scan velocity, (ii) nonlinear lateral scan velocity, and (iii) non-telecentric scan geometry.

* * * * *